United States Patent [19]
Scott

[11] Patent Number: 5,981,593
[45] Date of Patent: *Nov. 9, 1999

[54] PROSTAGLANDIN E2 TREATMENT OF IMPOTENCE

[76] Inventor: Nathan Earl Scott, 610 Laguna Rd., Fullerton, Calif. 92835

[*] Notice: This patent is subject to a terminal disclaimer.

[21] Appl. No.: 08/992,946

[22] Filed: Dec. 18, 1997

Related U.S. Application Data

[63] Continuation-in-part of application No. 08/090,483, Jul. 12, 1993, Pat. No. 5,708,031, which is a continuation of application No. 07/860,107, Mar. 30, 1992, abandoned, which is a continuation of application No. 07/725,350, Jul. 3, 1991, abandoned.

[51] Int. Cl.$^6$ .................................................. A61K 31/557
[52] U.S. Cl. ............................................................ 514/573
[58] Field of Search ............................................... 514/573

[56] References Cited

U.S. PATENT DOCUMENTS

| | | |
|---|---|---|
| 4,311,707 | 1/1982 | Birmbaum et al. . |
| 4,801,587 | 1/1989 | Voss et al. . |
| 4,955,878 | 9/1990 | See et al. . |
| 5,242,391 | 9/1993 | Place et al. . |

FOREIGN PATENT DOCUMENTS

| | | |
|---|---|---|
| WO 9002545 | 3/1990 | WIPO . |
| WO 9116021 | 10/1991 | WIPO . |

OTHER PUBLICATIONS

Andersen et a., Molecular Basis for Prostaglandin Potency, III. Tests of the Significance of the "Hairpin Conformation" in Biorecognition Phenomena, *Prostaglandins*, vol. 22, No. 5, pp. 841–855, Nov. 1981.

Artoux, Michelle J., "Alprostadil in Impotence," DICP, *The Annals of Pharmacotherapy*, 25:363–365, Apr. 1991.

Bernard et al., "The Roles of Urologist and Patient in Autoinjection Therapy for Erectile Dysfunction," *Contemporary Urology*, pp. 21–26, Jan./Feb. 1990.

Burnakis, Thomas, "Amyl Nitrite for the Treatment of Penile Tumescence," *Hospital Pharmacy*, vol. 26, 343–344, Apr. 1991.

Catanzarite, et al., "Prostaglandins: Mundane and Visionary Applications," Contemporary OB/GYN, pp. 21–41, Oct. 1987.

Cavallini, Giorgio, "Minoxidil vs. Nitroglycerine: A Perspective Double Blind Controlled Trial in Transcutaneous Erection Facilitation for Organic Impotence," *The Journal of Urology*, 146 :50–53, Jul. 1991.

Dray et al., "Prostaglandins of the E Series Inhibit Release of Noradrenaline in Rat Hypothalamus by a Mechanism Unrelated to Classical $\alpha_2$, Adrenergic Presynaptic Inhibition," *Neuropharmacology*, vol. 23 No. 4, pp. 457–462, 1984.

Dunn, C.D.R., "Prostaglandins and Erythropoiesis: Structure/Action Relationships and Identification of the Prostaglandin Responsive Cells," *Blut*, 42, pp. 307–314, 1981.

Ganong, William F., "Chapter 17, Energy Balance, Metabolism & Nutrition" pp. 229–231, *Review of Medical Physiology*, 85h Ed., 1977.

Ganong, William F., "Chapter 15. Instinctual Behavior & Emotions, Prostaglandins." p. 187 and Section IV. Endocrinology & Metabolism, Prostaglandins, p. 226, *Review of Medical Physiology*, 7th Edition, 1975.

Gauger et al., "Comparative Efficacy of Intravaginal Prostaglandin $E_2$ in the Gel and Suppository Forms for Cervical Ripening," DICP,*The Annals of Pharmacotherapy*, vol. 25, pp. 456–460, May 1991.

Larock et al., "Organopalladium Approaches to Prostaglandins, Synthesis of $PGF_{2\alpha}$ by the Controlled, One–Step, Palladium–Promoted, Intermolecular Coupling of Three Different Alkenes," *J. Am. Chem. Soc.*, 113, 7815–7816, 1991.

Lehinger, Albert, "The Molecular Basis of Cell Structure and Functionl," *Biochemistry*, Second Edition, 300, 686–687, 1975.

Pasargiklian et al., Clinical, Functional and Pathogenetic Aspects of Bronchial Reactivity to Prostaglandins $F_{2\alpha}$, $E_1$, and $E_2$, *Advances in Prostaglandin and Thromboxane Research*, vol. 1, pp. 461–475, 1976.

Takahashi et al., "Glomerular Actions of a Free Radical–Generated Novel Prostaglandin, 8–epi–Prostaglandin $F_{2\alpha}$, in the Rat," *J. Clin. Invest.*, vol. 90, 136–141, Jul. 1992.

Windholz, et al., Prostaglandin(s), *The Merck Index*, pp. 1134–1135, 1983.

Wolfson et al., "Intraurethral Prostaglandin E–2 Cram: A Possible Alternative Treatment for Erectile Dysfunction", *Urology*, vol. 42, No. 1, Jul. 1993 and *Abstract of Article*.

Zoutendam et al., "Quantitative Determinatin of Alprostadil ($PGE_1$) in Bulk Drug and Pharmaceutical For ulations by High–Performance Liquid Chromatography", 283, 273–280, 1984., "Prostin E–2," package insert of the Upjohn Company, revised Oct. 1990.

"Hemabat," package insert of the Uphohn Company, Nov. 1989.

"Impotence," *Medical Aspects of Human Sexuality*, pp. 66–68, May 1991.

*Primary Examiner*—William R. A. Jarvis
*Attorney, Agent, or Firm*—Koppel & Jacobs; Michael J. Ram

[57] ABSTRACT

The present invention relates to the treatment of impotence, and, more particular, to devices for the delivery of a clinically effective amount of prostaglandin $PGE_2$ through the urethral mucosa for the treatment of impotence. The device is a solid or porous wand coated with an effective amount of $PGE_2$ in a suitable carrier. The wand is sized for insertion into the urethra and the subsequent release and absorption of the $PGE_2$ through the urethral mucosa. In the alternative, the device is a tubular urethral insert through which a unit dosage of a liquid composition containing the $PGE_2$ is delivered.

10 Claims, 2 Drawing Sheets

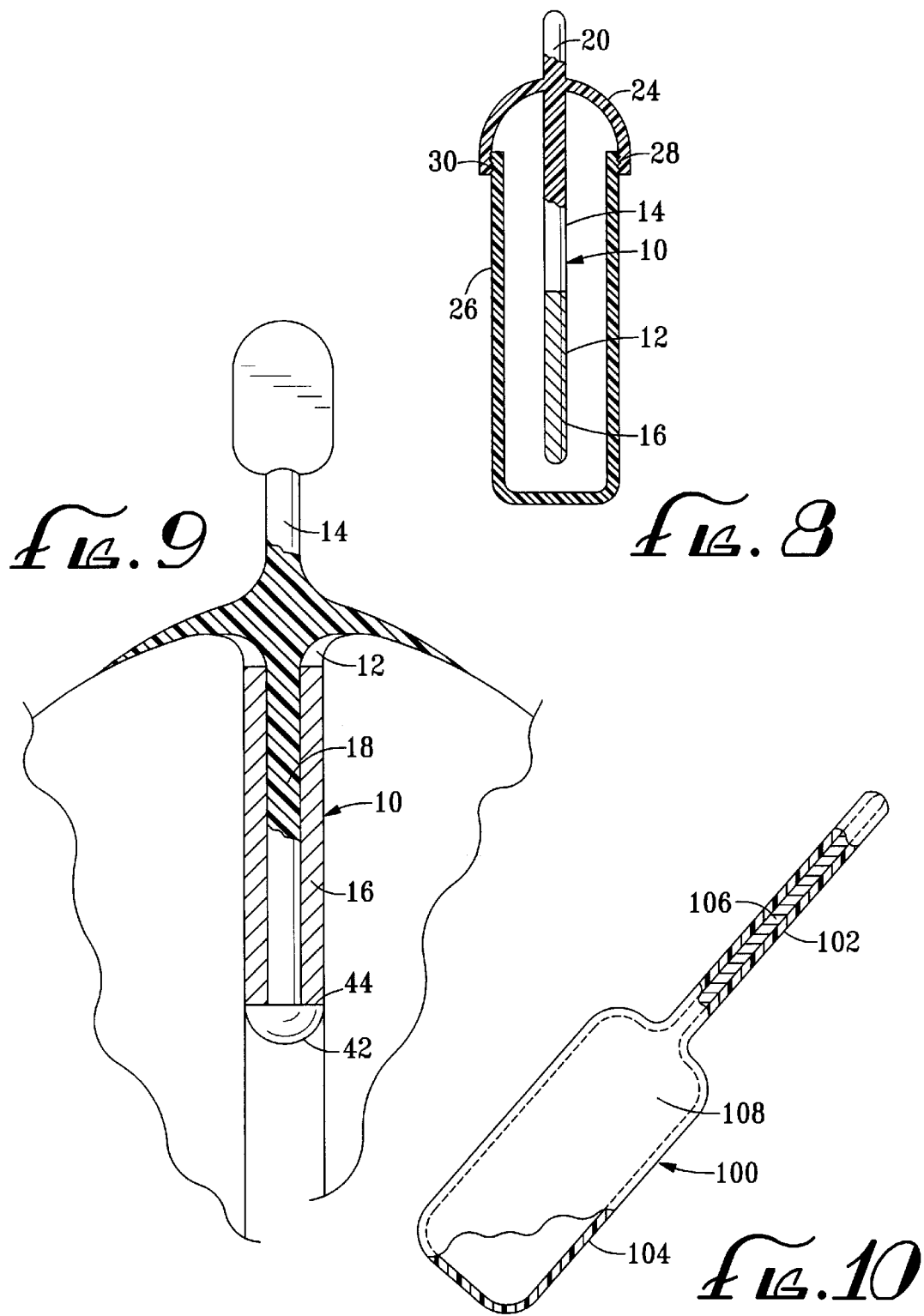

PROSTAGLANDIN E2 TREATMENT OF IMPOTENCE

BACKGROUND OF THE INVENTION

Area of the Art

This application is a continuation-in-part of Ser. No. 08/090,483, filed Jul. 12, 1993, now U.S. Pat. No. 5,708,031, which is a continuation of Ser. No. 07/860,107, filed Mar. 30, 1992, since abandoned, which is a continuation of Ser. No. 07/725,350, filed Jul. 3, 1991, now abandoned.

The present invention relates to the treatment of impotence, and, more particular, to devices for the delivery of a clinically effective amount of prostaglandin $PGE_2$ through the urethral mucosa for the treatment of impotence.

In excess of about 10 million men in the United States alone exhibit sufficient erectile dysfunction that they can be characterized as effectively impotent. A significant number of men additionally suffer from an inability to develop an erection which may not be diagnosed as impotence but may not be satisfactory to their desires or those of their partner to provide mutually satisfactory sexual intercourse. Impotence in the human male can arise from a variety of psychological and physiological etiologies. For example, long term diabetes, damage to the spinal cord, multiple sclerosis, or nerve damage resulting for example from lower abdomen or prostate surgery, and advancing age can result in impotence. For differing reasons, each of the foregoing result in an inability to pressurize the corpora cavernosa, which can result in turn from either an insufficient arterial inflow on the supply side, or an insufficient increase in the venous output resistance to blood flow.

A wide variety of mechanical means have been provided, in an effort to overcome erectile dysfunction. For example, U.S. Pat. No. 4,596,242 to Fischell discloses a surgically implantable hydraulic system, having a fluid reservoir and pressure generator, a patient manipulable valve, a pressure reservoir and a distensible member responsive to actuation of the valve. A variety of other prior art mechanical implants and other devices for this purpose are described in the Background of the Invention section of the U.S. Pat. No. 4,596,242.

In addition to the mechanical efforts to overcome erectile dysfunction, pharmaceutical approaches have been tried as well. For example, prostaglandin E1 has been observed to produce erection in some cases, but only by direct percutaneous injection into the penis (Artoux, M, DICP, *The Annals of Pharmacotherapy*, Apr. 25, 1991, p. 363–365) or by urethral placement of a meltable pellet containing $PGE_1$ (U.S. Pat. No. 5,242,391 issued Sep. 7, 1993 and WO 91/16021 published Oct. 31, 1991).

Notwithstanding the foregoing, there remains a need for an improved treatment of erectile dysfunction. Surgical implantation and/or repeated injections range from disfavored to medically disadvantageous, and do not, as a whole, provide a satisfactory solution to the problem. From a patient usability standpoint, erectile dysfunction would most advantageously be treated on a self-administration basis, without the need of surgical intervention or repeated injections of a pharmaceutical agent.

SUMMARY

In accordance with one aspect of the present invention, there is provided a method and device for treating erectile dysfunction in a male patient, comprising the step of administering to the patient a unit dose of a formulation comprising an erectile dysfunction treating amount of prostaglandin E2 ($PGE_2$) compound, or pharmaceutically acceptable salts or derivatives thereof. The prostaglandin E2 compound is preferably formulated together with a pharmaceutically acceptable delivery medium, which may comprise local anesthetic agents and/or a lubricant. Preferably, the anesthetic agent comprises lidocaine. The dose of $PGE_2$ may be in the form of a urethra sized suppository meltable at body temperature, coated on a removable wand, carried on and/or in a porous, non-absorbable wand sized for easy placement into and withdrawal from the urethra, or in physiologically acceptable carrier (saline) placed in the urethra via a small diameter tube.

A unit dose of the formulation in accordance with the present invention will typically be less than about 5 cc in volume, preferably less than about 3 cc and most preferably within the range of from about 1 cc to 2 cc. The amount of active ingredient in a unit dose will typically be within the range of from about 0.2 mg to about 5.0 mg. More preferably, the amount of prostaglandin E2 in a unit dose will be within the range of from amount 0.6 mg to about 1.8 mg in a formulation not also including lidocaine, and from about 1.2 mg to about 3.6 mg in a formulation including lidocaine.

The administration step of the method in accordance with the present invention comprises the transurethral placement of a unit dose of the formulation using the wand, suppository containing a quantity of the formulation suitable to deliver to the patient or a small diameter tube, within a suitable period of time.

In the embodiment of the present invention, wherein the administrable form of the formulation comprises a relatively rigid wand, the wand can be manually inserted into the distal opening of the urethra.

In accordance with a further aspect of the present invention, there has been provided a formulation and method for relieving the erectile dysfunction treating effects of the application of a formulation comprising prostaglandin E2, or of treating priapism of other etiology. In accordance with this antidote method, an effective antidotal amount of a formulation comprising a 15 methyl substituted prostaglandin $F2\alpha$ or pharmaceutically acceptable salt is administered in the same manner as described above.

These and further objects and advantages of the present invention will become apparent from the description which follows, considered together with the appended Claims.

BRIEF DESCRIPTION OF THE DRAWINGS

These and other features, aspects and advantages of the present invention will become better understood with reference to the following description, appended claims, and accompanying drawings, where:

FIG. 8 is a cut away side view of the third version of the insertable drug delivery device of FIG. 6 inserted in a carrier.

FIG. 9 is a cut away side view of a variation of each of the above versions inserted in a penis.

FIG. 10 is a partial cutaway view of a device for delivery of a liquid dose of impotence treating drug.

DESCRIPTION

Figure 1:
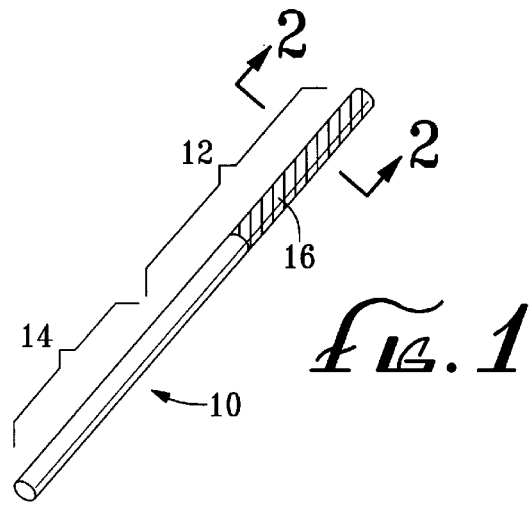
FIG. 1 is a perspective side view of a first version of the insertable drug delivery device.

The prostaglandins are a series of cyclic derivatives of certain unsaturated fatty acids. They are found in a variety of tissues, including the prostate gland, the seminal vesicles, the lungs and the brain. These naturally occurring prostaglandin are derived by cyclization of 20-carbon unsaturated fatty acids such as arachidonic acid. (Lehninger, Albert L., *Biochemistry*, 2d ed. (1975), p. 300 (hereinafter "Lehninger")).

Carbon atoms of the fatty acid backbone are cyclized to form a characteristic 5-membered ring. The prostaglandins are divided into a number of groups, including those designated A–F, based on the configuration of the ring structure. Prostaglandin also differ in stereochemistry and in the number of side chain double bonds which are conventionally indicated by a subscript number. Thus, for example, prostaglandin $E_2$ ("$PGE_2$") has the ring configuration characteristic of the E group and contains two side chain double bonds. The chemical name for $PGE_2$ is (5Z, 11α, 13E, 15S)-11, 15-Dihydroxy-9-oxo-prosta-5, 13-dien-1-oic acid and the structural formula of one form is represented in Formula I, below. The molecular formula is $C_{20}H_{32}O_5$.

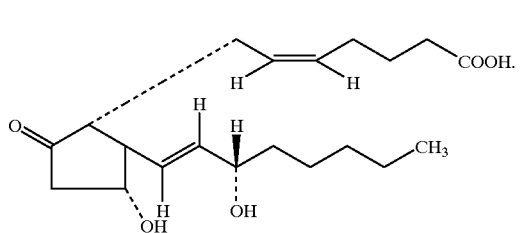

I

The biosynthesis of prostaglandin has been well characterized. See, e.g. Lehninger at p. 687. In a typical biosynthetic pathway, exemplified by production of $PGE_2$, the essential fatty acid linoleic acid is converted into the 20-carbon arachidonic acid, which is then acted upon by prostaglandin synthase, doxygenase enzyme. Oxygen atoms are added at carbon atoms 9 and 15, and the product is cyclized by formation of a bond between carbon atoms 8 and 12. In the presence of reduced glutathione, this cyclized product undergoes conversion into prostaglandin $E_2$. Other types of naturally occurring prostaglandins are derived from different polyunsaturated fatty acids.

In about the 1960's, prostaglandins were isolated from a particular species of Caribbean coral, which made them more widely available for research. (Catanzarite, Valerian A. and Gary Aisenbrey, *Contemporary OB/GYN* (October 1987), p. 22 (hereinafter "Catanzarite")). A large number of natural and synthetic analogues of the prostaglandins are now known. (Lehninger at 687).

The prostaglandins are known to produce often unpredictable effects over a very wide range of biological activities of a hormonal or regulatory nature. The various prostaglandin have been reported to both lower and raise blood pressure, to inhibit platelet aggregation and augment aggregation, to increase in some tissue and decrease in other tissue the cyclic AMP, to inhibit gastric secretion, dilate bronchi, inhibit lipolysis, antagonize vasopressin-induced anti-diarrhesis, constrict the pupil, increase and decrease the intraocular pressure and produce contraction of the uterus. (Ganong, William F., *Review of Medical Physiology*, 7th ed. (1975), p. 226 (hereinafter "Ganong")). The naturally occurring prostaglandins all appear to be capable of affecting the control of vascular and other smooth muscle contractions. In the central nervous system, prostaglandins are known to modify responses to certain synaptic transmitters. They have been reported to mimic the actions of some hormones and to inhibit the actions of certain others. (Ganong, p. 226.)

Two of the most extensively studied of the prostaglandin are $PGE_2$, and $PGF_{2\alpha}$. Both of these molecules are synthesized within the pregnant and non-pregnant uterus. While $PGE_2$ and $PGF_{2\alpha}$ are similar in mediating some effects, they are different with respect to certain others. Both cause uterine contractions, but they predominate at different sites within the uterus—$PGE_2$ in the lower uterine segment, $PGF_{2\alpha}$ is more important in generating uterine contractions. $PGE_2$ elevates body temperature, whereas $PGF_{2\alpha}$ has no apparent effect on body temperature. $PGE_2$ is a vasodilator and bronchodilator, while $PGF_{2\alpha}$ is a bronchoconstrictor and vasoconstrictor. (Catanzarite, p. 21–22).

Prostaglandins have been used in gynecology for pregnancy termination. Preparing the cervix with prostaglandin suppository has been found to reduce the incidence of cervical laceration and significant bleeding. (Catanzarite, p. 22). Synthetic analogues of prostaglandin $PGE_2$, such as 16-16-dimethyl $PGE_2$ and 9-methylene $PGE_2$, have proven useful for the induction of first trimester abortions. Such procedures typically use vaginal suppositories containing 20 milligrams $PGE_2$ or 3 milligrams 15-methyl $PGF_{2\alpha}$, or by repeated intramyometrial injections of 15-methyl $PGF_{2\alpha}$, or by infusing a $PGF_{2\alpha}$-urea mixture (20 milligrams of $PGF_{2\alpha}$ and 40 milligrams of urea in 100 Ml of 5% dextrose in water) into the amniotic sac.

In obstetrics, prostaglandins have been used for cervical ripening, labor induction and control of post-partum hemorrhage. (Catanzarite, p. 29). For cervical ripening, $PGE_2$ had been given intravenously, orally and vaginally, but the preferred route is intracervically. A $PGE_2$ gel is now commercially available in Scandinavia, and another $PGE_2$ gel is being investigated in the United States for Ob/Gyn applications. The $PGE_2$ gel can also be used for labor induction (3–5 mg of $PGE_2$, prepared by blending a 20 mg suppository with 60 mL of lubricating jelly and using 9–15 mL of the mixture, is placed in the vagina). (Catanzarite, p. 32). Prostaglandins have also been utilized to control post-partum hemorrhage.

Since circulating prostaglandin can be rapidly metabolized in the lungs, liver and kidneys, a number of synthetically modified prostaglandin have been developed that are not metabolized as quickly. (Catanzarite, p. 32).

Prostaglandin $E_2$, also known as the "Prostin E2" brand of "dynoprostone," or Prepidil® is available from Upjohn Company in the form of a vaginal suppository. Indications and usage reported by Upjohn are (i) termination of pregnancy from the 12th through the 20th gestational week, (ii) evacuation of the uterine contents in the management of missed abortion or intrauterine fetal death up to 28 weeks of gestational age, and (iii) in the management of non-metastic gestational trophoblastic disease (benign hydatidiform mole). (The Upjohn Co., Prostin E2 product description 810 994 009, October, 1990). Forest Labs provides Cervidil® for $PEE_2$ for similar purposes.

PGE$_2$ is also available from several sources as a purified, freeze dried product which is readily soluble in saline.

Contraindications to the use of PGE$_2$ include hypersensitivity to dynoprostone, acute pelvic inflammatory disease, or patients with active cardiac pulmonary renal or hepatic disease. Upjohn notes that although carcinogenic bioassay studies have not been conducted in animals for PGE$_2$ (because of the limited indication for use and the short duration of administration), there was no evidence of mutagenicity in either the Micronucleus Test or in the Ames Assay. Upjohn also indicates that a number of adverse reactions may be observed with the use of PGE$_2$ for abortions. These adverse reactions are related to the contractile effect of PGE$_2$ on smooth muscle and include vomiting, temperature elevations, diarrhea, nausea, transient diastolic blood pressure decreases, and a number of other effects. Upjohn's vaginal suppository contains 20 mg of PGE$_2$ in a mixture of glycerides of fatty acids.

Upjohn markets a (15S)-15-methyl analogue of prostaglandin PGF$_{2\alpha}$ under the brand name Hemabate®, also known as "carboprost tromethamine sterile solution." The structural formula of Hemabate® is represented in Formula II below:

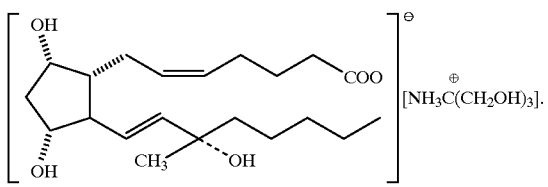

Upjohn reports that Hemabate® is indicated for aborting pregnancy between the 13th and 20th weeks of gestation, in certain condition related to second trimester abortions, and in the treatment of post-partum hemorrhage. (The Upjohn Co., product description 814 350 002, November, 1989). For abortion, the prostaglandin solution is injected using a syringe and administered deep in the muscle. Intramuscular injection is also used for treating post-partum uterine bleeding.

Upjohn also markets prostaglandin PGE$_1$, as the "Prostin VR Pediatric" brand of "alprostadil sterile solution," which is used to temporarily maintain the patency of the ductus arteriosus until corrective surgery can be performed in neonates having congenital heart defects and who depend upon the patent ductus for their survival. For the administration of PGE$_1$ in neonates, Upjohn recommends continuous intravenous infusion into a large vein, or administration through an umbilical artery catheter placed at the ductal opening. (The Upjohn Co., product description 811 987 004, in Physician's Desk Reference, 45th Edition, p.2250 (1991)).

Quite surprisingly, the inventor herein has discovered that transurethral application of PGE$_2$ can in many cases provide an effective, reversible treatment of erectile dysfunction in human males. Thus, in accordance with one embodiment of the present invention, PGE$_2$ or a pharmaceutically acceptable salt, ester or other derivative thereof is formulated together with or without a carrier medium which may comprise any of a variety of additional excipients or adjuvants. The composition is applied to a wand, which may be either porous or non-porous, in sufficient quantities so that the desired dosage is released and absorbed through the mucosa of the urethra when the coated wand is placed in the urethra. When an erection of the desired tumescence is obtained the wand is then removed, terminating delivery of the composition, thus significantly reducing the possibility of overdosing. While the formulation may be provided in the form of a meltable suppository, such a delivery means is unsuitable for removal to terminate delivery of the composition and can result in overdosing as well as the delivery of excess PGE$_2$ to the vagina of the partner.

In a second embodiment a suitable amount of a freeze dried PGE$_2$ is dissolved in physiological saline and placed within the urethra using a short, small diameter catheter. The PGE$_2$ absorption is rapid with an erection, ensuing within 3–5 minutes, persisting for 1–2 hours depending on dosage. However, alternative replacements for the saline include creams or gels which can flow at or above room temperature, for example at body temperature.

In accordance with another aspect of the present invention, there is provided an antidote for reversing the effects of the foregoing PGE$_2$ treatment, comprising administration of an antidotal amount of PGF$_{2\alpha}$, or pharmaceutically acceptable salts, esters or derivatives thereof. Preferably, 15-methyl PGF$_{2\alpha}$ is utilized for this purpose.

Although low viscosity gels or liquids may also be formulated, the liquid form also may present handling and delivery difficulties and may not present a sufficient dwell time in the urethra to permit absorption of an efficacious amount of the active ingredient or, in the alternative, delivery of the excess to the partner.

A typical male urethra on a flaccid penis is from about 2.5 cm to about 8 cm and the typical diameter of the urethra is from about 1 mm to about 3 mm. Accordingly, the wand with PGE$_2$ applied has a diameter approximating the urethra diameter or slightly larger so that the outer surface of the wand is in intimate contact with the mucosal lining of the urethra or swells when inserted. The typical length of the insertable portion of the wand is from 20% to 90% of the patients urethra in the flaccid state, preferred 25%–40% with some or all of the insertable portion coated with PGE$_2$. The wand also has an external portion or length for grasping between the users fingers for placement and removal. This portion may be of a larger diameter or a flange may be positioned between the insertable portion and the exterior portion to prevent the wand from being inserted too far into the urethra.

For delivery of the saline/PGE$_2$ solution, a catheter of about 1.5–3 mm is inserted into the urethra 0.5 to 2 cm and a bolus or spray of about 0.1 cc to 1 cc of a solution containing 0.1 to 2.0 mg PEG$_2$/0.1 cc is placed in the urethra.

The simplest embodiment of the drug delivery device, shown in FIG. 1, comprises a wand 10 which is sized to be placed within the urethra of the penis. The wand has an insertable portion 12 which, in use, resides in the urethra, and a holding portion 14 for grasping by the user during insertion. The insertable portion 12 has a partial or complete covering of PGE$_2$ in a suitable carrier 16.

Figure 2:
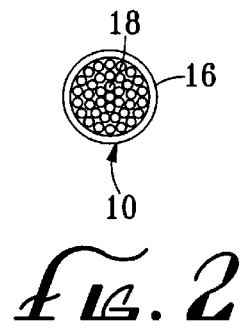
FIG. 2 is a cross sectional view taken along line 2—2 of FIG. 1.

FIG. 2 shows the wand 10 in cross section. The wand is shown as porous, with pores 18, the PGE$_2$, with or without a carrier, 16 being both on the surface of the wand 10 and in the pores 18. The invention contemplates a nonporous wand 10 with the PGE$_2$ and carrier coated only on the surface as well as an alternate porous version with the PGE$_2$ and carrier being on both the surface as well as in the pores. The porous version allows delivery of more drug to the patient. However, because some of the drug is within the pores, the delivery rate for that portion may be slower than for the $PGE_2$ in the surface coating.

Figure 3:
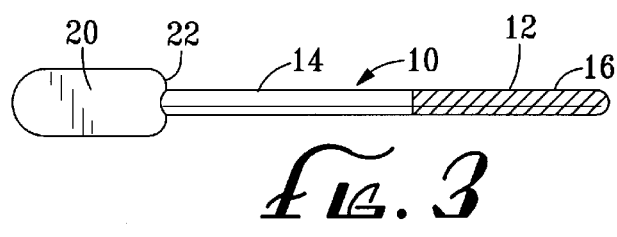
FIG. 3 is a side view of a second version of the insertable drug delivery device.
Figure 4:
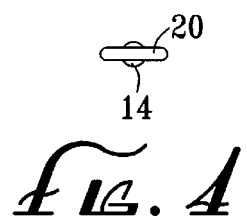
FIG. 4 is an end view of the second version of the insertable drug delivery device.

A second embodiment of the drug delivery device, shown in FIGS. 3 and 4, in addition to the features shown in FIGS. 1 and 2, has a handle 20 for grasping by the user during insertion and removal of the device. The shoulder 22 prevents the wand from being inserted to deeply.

Figure 5:
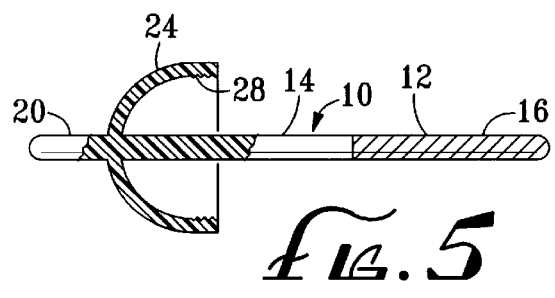
FIG. 5 is a side view of a third version of the insertable drug delivery device.
Figure 6:
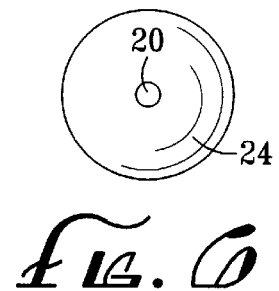
FIG. 6 is an left end view of the third version of the insertable drug delivery device.

A third embodiment, shown in FIGS. 5 and 6, instead of the shoulder 22, has an cap 24 to prevent insertion of the wand 10 to a depth greater than desired. In FIG. 5 the cap is shown to have a curved profile similar to the rounded shape of the head of the penis. However, any shape is usable as long as the width of the cap is greater than the diameter of the urethra so as to prevent insertion of more than the desired length. FIG. 6 shows the cap 24 as hemispherical in shape so that it can also serve as a cap to close a carrying container 26, such as shown in FIG. 8. In the particular embodiment shown in FIGS. 5, 6 and 8 the cap 24 has threads 28 on its lower inner surface which can interact with similarly disposed threads 30 on the outer upper end of the container 26. In this manner the drug containing wand 10 can be inserted in the container 26 and closed and sealed, such as by a sonic or heat weld, to keep the $PGE_2$ from contamination or dissipation. It is also contemplated that the threads 28 can be replaced by other sealing means such as snap rings or a friction fit, each of which may be further sealed by an externally applied adhesive tape (not shown).

Figure 7:
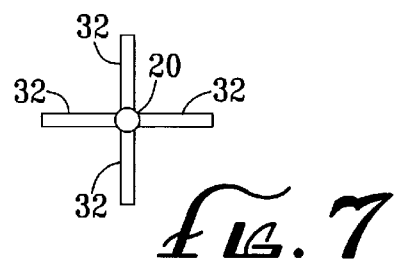
FIG. 7 is an left end view second variation of the third version of the insertable drug delivery device.

FIG. 7 shows a further variation of the embodiment of FIG. 5 wherein the cap 24 is replaced by one or more extensions 32 which radiate outward from the wand 20 at the juncture of the insertable portion 12 and the holding portion 16. FIG. 7 shows four extensions 32 which can be extended perpendicular to the want 10 surface or be curved as in FIG. 5.

FIG. 9 is an enlarged cut away view showing a further embodiment of the $PGE_2$ delivery device incorporating features shown in FIG. 7 placed within the male urethra. The porous wand 10 has the $PGE_2$ material in a suitable carrier 16 coated on the surface and in the pores of the wand. The insertion end of the wand 10 has a rounded tip 42 which has a diameter which approximates the diameter of the urethra. A length of the inserted portion 12 is coated with the $PGE_2$ and carrier composition 16, the composition or the $PGE_2$ alone also being carried in the pores 18 of the wand 10. As the PGE, coating melts or is absorbed, the diameter of the inserted coated portion decreases exposing the rear edge 44 of the rounded tip 42. As a result, when the wand 10 is removed from the urethra, the rear edge 44 acts as a wiper to remove excess $PGE_2$ and carrier from the urethra, thus substantially stopping the delivery of $PGE_2$ to the tissue of the penis. In this manner, the chance of overdose or transfer to the sexual partner during intercourse is greatly reduced or eliminated.

A delivery device 100 for the $PGE_2$ solution shown in FIG. 10 consists of a tube 102 with an integral squeeze bulb 104. The dimensions of the device are chosen so that a unit dose 106 of $PGE_2$ in a suitable solvent is held within the length of the tube and adjacent portion of the squeeze bulb 104 and the squeeze bulb 104 can contain a volume of air 108 such that squeezing of the bulb 104 between two fingers will expel the unit dose. When some or all of the tube is inserted through the external opening of the urethra, squeezing the bulb results in droplet or spray delivery of the tube's contents along at least a portion of the length of the urethra downstream of the inserted end of the tube 102. In one embodiment of the delivery device 100 the tube is from about 1.0 to 3.0 mm in length, has an outer diameter of about 2.5 mm and an inner diameter of about 1 mm. The tube is able to contain about 0.01 to 0.03 cc of liquid and the bulb is capable of delivering at least 0.01 cc of air when compressed. However, the tube inner and outer diameter may be smaller and a portion or all of the unit dose may be in the bulb. This allows retention of about 0.01 cc of a liquid in the lumen of the tube. Further, the delivery of the liquid composition is not limited to the use of the device of FIG. 10. One skilled in the art is knowledgeable in the selection of a broad range of catheters for placement within the urethra.

Administration of the $PGE_2$ may be accomplished by the transurethral placement of the wand to the desired depth. The $PGE_2$ composition applied to the wand depends on whether a porous or nonporous wand is used. In the case of a porous wand a liquid solution of the $PGE_2$, a carrier, and possibly an anesthetic and/or a transport adjuvant such as a meltable, swellable or soluble compound, is prepared and the wand is dipped in the solution until sufficient active material is deposited on and in the pores of the wand. This may be supplemented by a less fluid composition, with or without $PGE_2$, applied to the surface of the wand, the surface composition preferably including a lubricant or having lubricating properties.

Typically, a lubricant and/or a local anesthetic for desensitization will be provided for use as needed. In one embodiment, the $PGE_2$, lubricant and anesthetic are all formulated into a convenient cream for surface application. This composition may be prepared, for example, by mixing one Upjohn Prostin E® $PGE_2$ suppository together with 10 cc of a lidocaine jelly such as Xylocaine® 2% jelly (available from Astra Pharmaceutical Products) and 50 cc. of a surgical lubricant such as K-Y jelly (available from Johnson & Johnson) or suitable generic substitutes therefor. Lidocaine HCl, available in a variety of formulations, comprises acetamide, 2-(diethylamino)-N-(2,6-dimethylphenyl)-monohydrochloride. The composition is then coated onto the wand.

The amount of lubricant and the amount and concentration of anesthetic can be varied considerably as will be apparent to one of skill in the art. For example, lidocaine jelly can be used having anywhere from about 1% to about 10% and preferably about 2% lidocaine. In general, the anesthetic level can largely be dictated by patient preference, as determined through routine experimentation. Although the incidence of adverse effects with Xylocaine® 2% jelly is very low, caution should be exercised when applying large amounts since the frequency of adverse effects is directly proportional to the total dosage of the local anaesthetic administered. (Astra Pharmaceuticals, product description 021838 R11, June 1986; in Physician's Desk Reference, 45th Edition (1991), p. 628).

A variety of other anesthetic agents can also be used with the formulation of the present invention, as will be appreciated by one of skill in the art. For example, novocaine, procaine, tetracaine or benzocaine may be selected. Patients allergic to para-aminobenzoic acid derivatives such as procaine, tetracaine and benzocaine have not appeared to show cross sensitivity to lidocaine. Lidocaine is also contraindicated in patients with a history of sensitivity to amide type local anesthetics. Xylocaine® 2% jelly also contains methylparaben, propylparaben and hydroxypropylmethylcellulose, as well as lidocaine; and, therefor, Xylocaine® is contraindicated for patients with known sensitivities to any of these compounds. (Astra Pharmaceuticals, product description 021838R11, June 1986; in Physician's Desk Reference, 45th Edition (1991), p. 628).

It has been determined by the inventor that the effect of the PGE$_2$ treatment is generally less pronounced when delivered in a formulation which also comprises lidocaine. Thus, in a lidocaine-containing formulation, the dosage of PGE$_2$ is preferably increased over that in a non-lidocaine-containing formulation, and more preferably, the PGE$_2$ dosage is preferably doubled in a lidocaine-containing formulation.

More or less lubricant may be desired depending upon the delivery dose and concentration of the anesthetic. In general, the total volume of the impotence treating unit dose should be no more than 5 cc, and preferably from about 1 cc to no more than about 2 cc due to the inherent capacity of the urethra. Doses of excessive volume can result in painful administration, and also in retrograde migration of the excess formulation into the prostatic urethra or bladder.

Preferably, the total amount of PGE$_2$ contained in a unit dose will be within the range of from about 0.1 mg to about 5.0 mg. Due to differing etiology of erectile dysfunction, and inherent variations across a population in terms of responsiveness to pharmaceutical agents, some routine experimentation may be desired to determine optimum dosages for a given patient or class of patients.

In general, however, doses within the range of from about 0.5 to about 5.0, and preferably from about 0.6 to about 3.6 mg PGE$_2$ have generally proven sufficient in patients in which a response is likely to occur. For the purpose of the above the term unit dose designates the amount of PGE$_2$ which is delivered and transmitted through the urethral mucosa in a 15 minute period. One skilled in the art will recognize, depending on the speed of elution of the active material from the pores of a porous wand, the actual amount of PGE$_2$ on or in the wand will be greater than the actual amount delivered to and through the mucosa. Although it is not possible to predict with precision what types of patient populations will likely respond to the treatments disclosed herein, certain classes of patients are anticipated to be treatable depending upon the etiology of the condition. For example, patients in whom erectile dysfunction is associated with vascular abnormalities such as atherosclerosis which prevents adequate blood inflow are not likely to respond. Patients in whom the dysfunction is a result of such conditions as diabetes, denervation, postsurgically; i.e., following prostatectomy, or psychological status are expected to be more likely to respond.

In the use of the PGF formulation to treat priapism, the PGF will generally be present in an amount within the range of from about 5 to about 50 µg per 1 cc does of formulation, preferably within the range of from about 8 to 20 µg/cc and more preferably about 12 µg/cc. As with the PGE formulation, optimum dosage for a given patient can be determined through routine experimentation.

Alternatively, a composition meltable at body temperature, such as used in a suppository may be applied to the surface of the wand 10. Once placed in the urethra, under influence of body temperature, the composition melts and allows delivery of the PGE$_2$. However, an advantage of applying the meltable composition to the surface of the wand is that the wand can be removed once the desired erection is achieved, thus terminating drug delivery, a procedure not afforded by suppository products. Alternatively, the PGE$_2$ composition placed in the pores of the wand can be protected until delivery by applying a sealing material on the surface of the wand, the sealing material melting or dissolving when placed within the urethra. As a further alternative, materials can be used which will dissolve or swell in an aqueous environment at a pH within the range of that typical of the urethra. One suitable composition is a mixture of glycerides of fatty acids such as that used with the Prostin E2® product. Other suitable compositions include various cellulose based materials such as hydroxypropylmethylcellulose or collagen compositions which can be prepared as a fluid water-based material, a viscous solution, a gel or a water swellable dry coating. One skilled in the art can identify numerous physiologically acceptable water soluble materials or hydrogels which can be used for the purposes set forth above.

A major advantage of transurethral insertion of a wand is that it can be inserted for a predetermined period of time and then removed following delivery of an efficacious amount of drug. The removable time release delivery structure has the added advantage of providing a range of flexibility in the total delivered dose. Thus, the patient, by leaving the implant in place for relatively shorter or longer periods of time, can optimize the dose within a preset maximum range. A particular advantage of the cream, gel, or solution over prior disclosed pellets of drug containing compositions placed in the urethra is that the compositions disclosed herein can be readily dispersed along the length of the urethra allowing delivery through a large area of tissue surface, thus reducing or eliminating the undesirable effects of delivering high dose concentrations to a very localized area, including slower dispersion, localized discomfort and less pronounced effectiveness.

Particular embodiments of the present invention will be described in the Examples which follow.

EXAMPLE I

Preparation of Intraurethral PGE$_2$ Cream

A batch of PGE$_2$ cream was prepared by mixing two 20 mg PGE$_2$ suppository (obtained as the "Prostin E2" suppository from the Upjohn Company) with 10 cc of 2% Xylocaine jelly and 50 cc of K-Y surgical lubrication jelly (hydroxyethyl-cellulose, obtained from Johnson & Johnson). Mixing was accomplished by stirring until the mixture appeared homogenous upon visual inspection. The result was a PGE$_2$ cream having approximately 1.3 mg of PGE$_2$ per 2 cc of cream. Approximately 2 cc of cream was applied to a 4 cm of the insertable length of a porous wand to produce a coated product 5 mm in diameter. This can be readily inserted and removed from the urethra.

EXAMPLE II

Preparation of Intraurethral PGE$_2$ Gel

The homogenicity of a batch of PGE$_2$ is ensured by inclusion of a methylene blue marker. One 20 mg PGE$_2$ suppository ("Prostin E2" from the Upjohn Company) is sliced into thin slices and allowed to soften at room temperature for 15 minutes. A small drop of 1% methylene blue solution (American quinine, Shirley, N.Y.) is placed onto each slice to serve as a marker for homogenicity. The softened slices are thereafter geometrically mixed with the contents of a 56.7 gram tube of K-Y jelly to yield a homogenous mixture, as evidenced by blue color uniformity. The theoretical content of the final product is approximately 0.68 milligrams of PGE$_2$ per 2 cc of gel. The gel was applied to 4 cm of the insertable length of a porous wand to produce an insertable product having a 3.0 to 5.0 mm diameter for insertion in the male urethra.

EXAMPLE III

Preparation of Lipid Based Intraurethral PGE$_2$ Meltable Cream

A batch of PGE$_2$ cream in cocoa butter is prepared by placing one 20 mg. PGE$_2$ suppository (Prostin E2 by the Upjohn Company) into a porcelain evaporating dish and is melted in a 37° C. water bath. Shredded cocoa butter is added to the melted suppository with stirring to bring the total mass to approximately 20 grams. As the melting continues, the temperature of the mixture is kept at or below about 33° C. Higher temperatures are to be avoided, as they have been reported to cause the crystalline form of the cocoa butter to change, resulting in aberrations in bioavailability. Transformations in the crystalline form of the cocoa butter are visually observed as a change from opalescent to transparent. After complete melting, the mixture is applied to 4 cm of the insertable length of a porous wand which was about 2 mm in diameter using a tubular mold. The material is thereafter allowed to cool at room temperature for about 15 minutes, and thereafter is placed in the refrigerator to facilitate further solidification in to 5 mm diameter coated wands. The coated wands are thereafter removed from the mold, individually packaged and placed in refrigerated storage under anhydrous conditions.

EXAMPLE IV

Administration of Intraurethral $PGE_2$

Wands containing about 2 cc of a $PGE_2$ composition prepared in accordance with Examples I–III placed within the urethra of males would be expected to cause full tumescence suitable for intercourse in a majority of the test subjects within about 5 minutes of placement of the wand at which point the wand can be removed, such removal terminating the delivery from the wand of the $PGE_2$, except for small amounts which remain on the urethral mucosa.

EXAMPLE V

Efficacy of Lower Concentrations of $PGE_2$ Cream in Treating Human Erectile Dysfunction Meltable $PGE_2$ cream and gel inserts were prepared in accordance with Examples I–III and administered in accordance with the procedures of Example IV, except that a 10 mg $PGE_2$ (Prostin) instead of a 20 mg suppository. The wand contained approximately 0.7 mg of $PGE_2$ per 2 cc of cream or gel. The lower concentration containing wand was used to treat each of ten impotent men between the ages of 50 and 70. After 15 to 30 minutes, treatment response was rated as no penile tumescence, partial tumescence, or full tumescence.

As a result, four of the ten men treated had no response, two had partial tumescence, and four had full tumescence. Thus, even using lower concentrations of $PGE_2$, 60% of the men treated showed at least partial penile tumescence in response to the intraurethral $PGE_2$ cream.

EXAMPLE VI

Intraurethral Administration of a $PGE_2$ Hydrogel Composition

A wand carrying approximately 5 mg of $PGE_2$ in a hydrogel polymer carrier was placed into the urethral meatus of a 65 year old impotent male patient.

An effective erection resulted after 15 minutes at which point the wand was removed. Erection was sufficiently effective for intercourse. Detumescence commenced at approximately 1 hour after removal. Some $PGE_2$ remained in the wand after removal, the amount not being ascertained. As a result, an amount of $PGE_2$ less than 5 mg was delivered.

EXAMPLE VII

Administration of $PGE_2$ from Solution

Freeze dried $PGE_2$ was obtained from Chinoin Pharmaceutical and Chemical Works Co. Ltd., Budapest, Hungary. Three different solutions were prepared with $PGE_2$ concentration being 0.5, 0.75 or 1.0 mg/0.1 cc of physiological saline. 0.1 cc of a solution containing 0.75 mg of $PGE_2$ was placed in the bulb and insertable portion of a 2.5 mm OD/1 mm ID tube, the open end of the tube was inserted about 1 cm into the urethra of a male patient and the contents of the tube rapidly expelled into the portion of the urethra in front of the inserted tube. The $PGE_2$ solution coated a portion of the remaining length of the urethra and the $PGE_2$ was rapidly absorbed through the mucosa of the urethra. Depending on the patient, an erection suitable for intercourse formed in 3 to 5 minutes and lasted for about one hour. When tried on the same patient, higher concentrations and larger volumes of the same concentration resulted in a more rapid formation of an erection and the effect lasted longer. Conversely, decreasing the concentration or the volume of a specific concentration had a lesser effect. The effectiveness of the composition also depended on the physiological cause of the impotence. However, generally speaking the effect was more pronounced, rapid and longer lasting then a similar quantity of $PGE_1$ provided by currently available commercial products or the compositions set forth in Examples I–VI above. It was also found that the initial burning sensation encountered when certain of the above described compositions or prior compositions were used did not occur. As a result, inclusion of an anesthetic such as lidocaine or Xylocaine was not needed. This allowed a more effective response with the same amount of $PGE_2$ or required for less $PGE_2$ for the same response.

Although the present invention has been described in considerable detail with reference to certain preferred versions and uses thereof, other versions and uses are possible. Therefore, the spirit and scope of the appended claims should not be limited to the description of the preferred versions contained herein.

What is claimed is:

1. A delivery system for treating erectile impotence by delivery of a unit dose of an effective amount of a physiologically active composition to the mucosa of a male urethra comprising:

a urethral placement device containing the physiologically active composition, said device having at least a portion cylindrical in shape with an outer diameter approximating the diameter of the urethra and a length which limits insertion into the urethra to a predetermined depth;

the physiologically active composition being a compound having a structural formula:

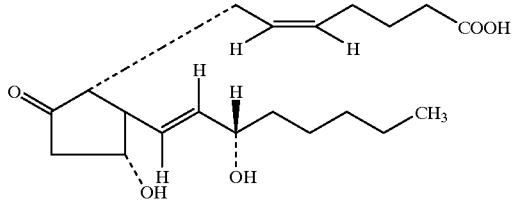

or a physiologically acceptable salt or ester thereof, said physiologically active composition carried in a readily dispersable pharmaceutically acceptable delivery medium which allows a maximized, preferred localized effect.

2. The delivery system for treating erectile impotence of claim 1 comprising a rod with the physiologically active composition in combination with the pharmaceutically acceptable delivery medium coated on the outer surface thereof.

3. The delivery system for treating erectile impotence of claim 2 wherein the rod contains pores therein, the pores being open to the surface of the rod, the physiologically active composition also being located in the pores such that it is transportable to the surface of the rod by the pharmaceutically acceptable delivery medium.

4. The delivery system for treating erectile impotence of claim 2 wherein the pharmaceutically acceptable delivery medium is selected from the group consisting of a material meltable at body temperature, a water soluble polymer and a water swellable polymer.

5. The delivery system for treating erectile impotence of claim 4 wherein the pharmaceutically acceptable delivery medium is selected from the group consisting of methylparaben, propylparaben, hydroxypropylmethylcellulose, glycerides of fatty acids, collagen, hydroxyethylcellulose and cocoa butter.

6. The delivery system for treating erectile impotence of claim 3 wherein the pharmaceutically acceptable delivery medium is selected from the group consisting of a material meltable at body temperature, a water soluble polymer and a water swellable polymer.

7. The delivery system for treating erectile impotence of claim 6 wherein the pharmaceutically acceptable delivery medium is selected from the group consisting of methylparaben, propylparaben, hydroxypropylmethylcellulose, glycerides of fatty acids, collagen, hydroxyethylcellulose and cocoa butter.

8. The delivery system for treating erectile impotence of claim 1 comprising a tube with means attached thereto for expelling material held within the tube into and along at least a portion of the length of the urethra, said material being a liquid comprising the physiologically active composition dissolved in the pharmaceutically acceptable delivery medium, said pharmaceutically acceptable delivery medium capable of flowing at body temperature.

9. The delivery system for treating erectile impotence of claim 8 wherein the pharmaceutically acceptable delivery medium is liquid at body temperature.

10. The delivery system for treating erectile impotence of claim 8 wherein the pharmaceutically acceptable delivery medium is liquid at room temperature.

* * * * *